United States Patent [19]

Duermeyer

[11] 4,292,403
[45] Sep. 29, 1981

[54] DETECTION AND/OR DETERMINATION OF IGM, IGA, IGD AND IGE IMMUNOGLOBULINS

[75] Inventor: Willem Duermeyer, OSS, Netherlands

[73] Assignee: Akzona Incorporated, Asheville, N.C.

[21] Appl. No.: 67,680

[22] Filed: Aug. 20, 1979

[30] Foreign Application Priority Data

Aug. 24, 1978 [NL] Netherlands .......................... 7808730

[51] Int. Cl.$^3$ ....................... G01N 33/54; C12Q 1/70; G01N 33/16; C12N 9/96
[52] U.S. Cl. .......................................... 435/5; 435/7; 435/177; 435/188; 435/810; 23/230 B; 252/408; 424/1.5; 424/8; 424/12
[58] Field of Search ....................... 435/5, 7, 177, 188, 435/810; 23/230 B; 252/408 R; 424/1, 1.5, 8, 12

[56] References Cited

U.S. PATENT DOCUMENTS

| | | | |
|---|---|---|---|
| 3,514,859 | 6/1970 | Peterson | 32/2 |
| 3,551,555 | 12/1970 | Schuurs | 424/12 |
| 3,553,310 | 1/1971 | Csizmus et al. | 424/12 |
| 3,555,143 | 1/1971 | Axen et al. | 424/1 |
| 3,639,558 | 2/1972 | Csizmus et al. | 424/12 |
| 3,867,517 | 2/1975 | Ling | 23/230 B |
| 3,966,898 | 6/1976 | Sjöquist et al. | 424/1.5 |
| 4,036,945 | 7/1977 | Haber | 424/1 |
| 4,041,146 | 8/1977 | Giaever | 424/1 |
| 4,092,114 | 5/1978 | Buck | 23/230 B |
| 4,098,876 | 7/1978 | Piasio et al. | 23/230 B |
| 4,166,106 | 8/1979 | Sedlack et al. | 435/7 |
| 4,235,869 | 11/1980 | Schwarzburg | 424/8 |

FOREIGN PATENT DOCUMENTS

1022459 12/1977 Canada.
2163318 11/1978 Fed. Rep. of Germany.

OTHER PUBLICATIONS

Kato, et al., "Enzyme-linked Immunoassay: Conjugate of the FAB Fragment of Rabbit IgG with B-D-Galactosidase from E. Coli and Its Use for Immunoassay", *J. Immunol*, vol. 116, No. 6, (1976), pp. 1554–1560.
Schuurs, et al. "Enzyme-Immunoassay", *Chn Chem. Acta*, vol. 81 (1977) pp.1–40.
Hamaguchi et al., "Enzyme-Linked Sandwich Immunoassay of Macromolecular Antigens Using the Rabbit Antibody-Coupled Glass Rod as a Solid Phase", *Eur. J. Biochem.*, vol. 71, (1976), pp. 459–467.
Lind, "Occurrence of Protein A in Strains of *Staphylococcus Aureus* Demonstrated by Means of Labelled Globulins", *Contributions to Microbrol & Immunol*, vol. 1, (1973), pp. 93–97.
Kronvall et al., "Differences in Anti-Protein A Activity Among IgG Subgroups", *J. Immunol*, vol. 103 (1969), pp. 828–833.
Forsgren, et al., "Protein A From S. Aureus", *J. Immunol*, vol. 97, No. 6, (1966), pp.822–827.
Jensen, *Unders belser Over Stalylococcus Antigenstruktur*, Ejnnr Munksgaard, Copenhagen, (1959), p. 98.
Forsgren, et al. "Protein A Mutants of *Staphylococcus Aureus*", *J. Bact.*, vol. 107, No. 1, (1971), pp. 245–250.
Stalenheim et al., "Protein A From *Staphylococcus Aureus*", *J. Immunol*, vol. 105, No. 4, (1970), pp. 944–948.
Kronvall, *Chem. Abstracts*, vol. 67, (1967), No. 72002(h).
Nickerson, *Chem. Abstracts*, vol. 73, (1970), No. 53153(u).
Jonsson et al., "The Use of Protein-A Containing *Staphylococcus Aureus* as a Solid Phase Anti-IgG Reagent in Radioimmunoassays as Exemplified In the Quantitation of α-X-feto-protein In Normal Human Serum", *Evr J. Immunol*, vol. 4, (1974), pp. 29–33.
Kronvall et al., "Definition of Staphylococcal Protein A Reactivity for Human Immunoglobulin G. Fragments", *Immunochem*, vol. 7, (1969), pp.124–127.
Williams et al., "Cellular Reactions with Protein A of Staphylococcus Aureus", *P. S. E. B. M.*, vol. 139, (1972), pp.480–483.
Christensen et al. "New Method for the Serological Grouping of Streptococci with Specific Antibodies Adsorbed to Protein A-Containing Staphylococci", *Infection and Immunity*", vol. 7, No. 6, (1973), pp. 881–885.
Lind, et al., "Electron Microscopy of Staphylococcal Protein A Reactivity and Specific Antigen-Antibody Reaction", *Acta Path. Microbiol. Scand.*, Sec. B, vol. 80, (1972), pp.281–291.
J. Reiss, "The Immunofluorescence Adsorption Test (IFAT) in the Estimation of Staphyloccal Protein A, " Contributions to Microbiology and Immunology, vol. I, Staphylococci and Staphylococcal Infections, p. 98 (Darger, Basel, 1973).
A. Forsgren et al., "Protein A from Staphylococcus Aureus," *Acta. Path. Microbiol. Scand.* 75 at 466-480 (1969).

*Primary Examiner*—Thomas G. Wiseman
*Attorney, Agent, or Firm*—Robert H. Falk; Charles A. Wendel; Francis W. Young

[57] ABSTRACT

The present invention relates to (1) a method for the detection and/or determination of an antigen specific immunoglobulin of a peculiar IgX class, in which X means M, A, D or E, comprising: (a) contacting and reacting the test-medium with either insolubilized anti-IgX against the antigen specific immunoglobulin of a peculiar IgX class to be determined, or antigen binding fragment of this anti-IgX, (2) incubating said contacted and reacted test medium with an antigen for which the immunoglobulin to be determined has specific affinity, and with a labelled antigen binding fragment of an antibody against said antigen, as well as (2) the novel coupling product comprising an antigen immunochemically bound to a labelled antigen binding fragment of an antibody against said antigen, and (3) test kit for the performance of said method (1). The labelling agent is detected and/or determined, which provides qualitative and/or quantitative information about the antigen specific immunoglobulin to be determined.

31 Claims, No Drawings

DETECTION AND/OR DETERMINATION OF IGM, IGA, IGD AND IGE IMMUNOGLOBULINS

BACKGROUND TO THE INVENTION

1. Field of the Invention

The invention relates to (1) a method for the detection and/or determination of an antigen specific immunoglobulin, to (2) a novel reagent and to (3) test kits for use in such determinations.

2. Description of the Prior Art, and Other Information

The immunoglobulins can be subdivided into five classes G, A, M, D and E. Immunoglobulins of these classes are indicated with IgG, IgA, IgM, IgD, and IgE respectively. In the following, immunoglobulins of a certain class will be indicated with IgX, in which X means, A, M, D and E for purposes of this invention.

Immunoglobulins are structurally related and contain at least two heavy chains (H-chains) and two light chains (L-chains), which are mutually connected by disulphide bridges and sometimes via additional polypeptides. The heavy and light chains each have a variable and a constant region. Some immunoglobulins consist of a multiple of the basic structure of two heavy and two light chains.

Antibodies are immunoglobulins, which can bind antigens specifically. The antibody specificity is located in the variable regions of the 4 peptide chains, which are all situated at the same side of the molecule (N-terminal side). A number of biological actions of a certain antibody is mediated through the constant regions of the chains of the immunoglobulin molecule concerned.

Antibodies can be cleaved into fragments, which still have antigen specifity and crystallizable fragments without this antigen binding property. Antigen binding fragments are e.g. Fab-, Fab'- and F(ab')$_2$-fragments. Crystallizable fragments without antigen specifity are e.g. Fc- and Fc'-fragments.

The concentration of immunoglobulins of the several classes in normal human serum is: IgG 8–16 mg/ml, IgA 1.4–4 mg/ml, IgM 0.5–2.0 mg/ml, IgD 0.0–0.4 mg/ml and IgE 0.000017–0.000450 mg/ml.

Quantitatively antibodies of the IgG class constitute therefore the most important group of antibodies. Antibodies of the IgM class are present in the early stages of an infection, so that determination of antibodies of the IgM class is very important for the early detection of an infectious disease.

Antibodies of the IgA, IgD and IgE classes can be present in serum in increased concentration in certain pathological conditions. For example, antibodies of the IgE class are present in increased concentrations in allergic conditions and antibodies of the IgD class are involved in auto-immune diseases.

The determination of antigen specific immuno-globulins of a peculiar class is of particular clinical significance. Antigen specific immunoglobulins can be determined with immunochemical techniques, in which use is made of an immuno component with binding affinity to the antibody to be detected and/or determined. According to a known technique, an immuno component with binding affinity to the antibody to be determined is made insoluble by coupling to a solid carrier and another specific bindable substance is labelled, for example with a fluorescent, chromophoric or radio-active group or with an enzyme. A disadvantage of these techniques is, that if the rheumatoid factor (RF) is present, which is often present in serum, false positive reactions may be obtained.

Furthermore, the methods for separation of immunoglobulins of different classes and especially of antigen specific immunoglobulins of different classes are elaborate and time consuming and give generally only qualitative or semi-quantitative results. Examples of these methods are immuno-diffusion, immuno-electrophoresis and sucrose density gradient centrifugation.

The rheumatoid factor which often causes false-positive results, is itself also an immunoglobulin, usually of the IgM class. The rheumatoid factor (RF) has affinity for antibodies of the IgG class. RF binds via the constant regions of the heavy chains of the IgG molecule and especially that part, which upon cleavage of the antibody is separated from the antigen binding fragments. Because the rheumatoid factor is usually of the IgM class, it will also be bound by anti-IgM immunoglobulins.

SUMMARY OF THE INVENTION

The invention now relates to a method for the determination of an antigen specific immunoglobulin of a peculiar IgX class, in which interference of the rheumatoid factor is avoided as well as a novel coupling product used in said method, and a test kit for the performance of said method.

According to the method of the invention, the serum in which an antigen specific immunoglobulin of a peculiar IgX class is to be detected and/or determined, is brought into contact with an insolubilized antibody against the antigen specific IgX concerned or an antigen binding fragment of this anti-IgX. An incubation is subsequently performed with an antigen for which the immunoglobulin has specific affinity, after which a further incubation takes place with a labelled antigen binding fragment of an antibody against the above-noted antigen.

DESCRIPTION OF THE PREFERRED EMBODIMENTS

The fragmentation of an antibody into crystallizable and antigen binding fragment of fragments may be effected by enzymatic cleavage of the heavy chains or by enzymatic cleavage of these chains and subsequent chemical cleavage of the obtained antigen binding fragment into two smaller antigen binding fragments.

For example, by enzymatic cleavage with papain, two identical monovalent antigen binding Fab-fragments and a crystallizable Fc-fragment without antigen binding properties are obtained. By enzymatic cleavage with pepsin, a divalent antigen binding F(ab')$_2$-fragment is obtained, which can be chemically cleaved into two Fab'-fragments.

Although RF is possibly bound by the insolubilized anti-IgX and may be bound directly or indirectly by insolubilized antigen binding fragment of this anti-IgX, a labelled antigen binding fragment of an antibody will not be bound by the RF. In this way false-positive reactions due to the RF will be avoided. The incubation with antigen and the subsequent incubation with labelled antibody fragment may also be performed in one step by using as reagent a previously labelled antigen, whereby labelling has been effected by coupling this antigen with the labelled antibody fragment. Such a reagent is novel and the invention therefore also relates to these new reagents, consisting of a coupling product of an antigen with a labelled antigen binding part of an antibody against this antigen. By use of this new reagent, intensive purification of the antigen is not necessary, which is a substantial advantage.

As stated above, the method according to the present invention may be used for qualitative and quantitative determination of an antigen specific immunoglobulin of each of the five IgX classes separately, without the occurrence of false-positive reactions due to the rheumatoid factor.

The solid carrier to which the anti-IgX or antigen binding fragment of this anti-IgX is coupled may be any water-insoluble solid carrier where coupling is effected by means of covalent bonds or by means of adsorption. The solid carrier may be in the form of granules or strips of various shapes and size. It may also be a tube or a micro-titration plate, in which the immunochemical reaction is performed, whereby the anti-IgX component is coupled to the inner surface of the reaction vessel.

The antigen binding fragment of the antibody with affinity to the antigen to be used may be labelled with enzymes or with fluorescent, chromophoric or radioactive groups or atoms. Use is preferably made of enzyme labelling. Examples of enzymes include catalase, peroxidase, urease, glucose oxidase and phosphatase, but many other enzymes are possible. After conclusion of the immunochemical reaction, an enzyme substrate is added to the liquid and/or solid phase of the reaction mixture obtained, after which an enzyme determination is performed, for example colorimetrically, fluorimetrically or spectrophotometrically.

The invention also relates to test kits, to be used in the method according to the determination.

The test kit is composed predominantly of the following components:

(a) a certain quantity of an insolubilized anti-IgX or antigen binding fragment of this anti-IgX, (b) a certain quantity of an antigen, against which the IgX to be determined is directed, (c) a certain amount of a labelled antigen binding fragment of an antibody against the antigen referred to in (b).

The labelled antibody fragment referred to in (c) may preferably be labelled with an enzyme.

In that case, the test kit also contains a substrate for the determination of the amount of the enzyme used.

Instead of the separate components (b) and (c), the test kit may also contain a single reagent, namely a coupling product of an antigen with a labelled fragment of an antibody against this antigen.

The invention is further illustrated by means of the following examples.

EXAMPLE I

Determination of IgM antibodies against hepatitis A virus/antigen

A. Preparation of animal anti-human IgM

Rabbit anti-human IgM was prepared according to a method described by R. Gispen, J. Nagel, B. Brand-Saathof and S. de Graaf, Clin. Exp. Immunol. 22, 1975, 431–437.

The specificity of the anti-IgM was increased by absorbing the anti-IgM serum with human umbilical cord serum for removal of anti-IgG.

0.05 ml umbilical cord serum was added to 0.2 ml anti-IgM serum and the mixture was incubated for 1 hour at 37° C. It was then centrifuged at 14000 g for 20 minutes. The supernatant was kept at 4° C.

B. Preparation of hepatitis A virus/antigen

A 20% extract was prepared from a faecal sample containing hepatitis A. 1 g faeces was mixed with 4 ml 0.005 M phosphate buffer, pH 7.2 (PBS) and 4 ml chloroform, and the whole was shaken vigorously for 5 minutes. The suspension was then centrifuged at 3000 g for 30 minutes at 4° C. The aqueous phase was pipetted off and kept at −20° C. When necessary, an amount of 20% extract was diluted in PBS such that an extinction of about 1.00 was obtained with the diluted extract in the sandwich enzyme immuno-assay for the determination of hepatitis A antigen, as described by W. Duermeyer, J. v.d. Veen and B. Koster, Lancet 1978, I, 823.

C. Preparation of F(ab')$_2$-fragments of IgG against hepatitis A

IgG was isolated from whole serum obtained from a hepatitis A patient by fractionation on DEAE-Sephadex in 0.0175 M phosphate buffer, pH 6.3.

A solution (1%–3%) of IgG in Walpole's acetate buffer (pH 4.3) was preheated at 37° C. during 20 hours.

Pepsin, dissolved in the same buffer, was added to give an enzyme: substrate ratio of 1:100.

The mixture was incubated at 37° C. for 20–24 hours.

The reaction was stopped by the addition of TRIS salt to adjust the Ph to 8.

The fragments were separated on a Sephadex G 150 column in 0.1 M Tris/HCl, pH 7.7, +0.2 M NaCl, +2 mM EDTA.

D. Preparation of enzyme-labelled F(ab')$_2$ conjugate

The F(ab')$_2$ conjugate against hepatitis A virus/antigen was prepared according to the method of P. K. Nakane and A. Kawaoi, J. Histochem. Cytoch., 22 (12), 1974, 1084–1091.

5 mg horse-radish peroxidase was dissolved in 1 ml 0.3 M carbonate buffer, pH 8.1 and 0.1 ml fluoro-dinitrobenzene, 1% in absolute alcohol, was added, followed by 1 ml 0.08 M sodium periodate.

The reaction was stopped with 1 ml 0.1 M ethylene glycol.

After dialysis against 0.01 M carbonate buffer, pH 9.5, 5 mg F(ab')$_2$ was added. This F(ab')$_2$ had previously been dialysed against 0.005 M PBS, pH 8.0.

After a reaction time of 2½ hours at room temperature, the solution was dialysed overnight at 4° C. against 0.005 M PBS, pH 8.0

The conjugate was kept at 4° C.

E. Determination of IgM antibodies against hepatitis A

The following test system was set up:

I. Coating.

The wells of microtitration plates were coated by incubation with 5 μg IgG (anti-IgM) per ml in 0.05 M phosphate buffer pH 7.2 (PBS) for 16 hours at room temperature.

The plates were then washed 3× with PBS+0.05% Tween 20 (PBS/Tween).

II. Test serum.

0.125 ml of a serum dilution in PBS/Tween was pipetted into the wells and incubated at 37° C. for 4 hours, followed by washing 3× with PBS/Tween.

III. Antigen.

0.1 ml antigen solution, in the working dilution, was added to each well. The plate was incubated overnight at room temperature, after which it was washed 4× with PBS/Tween.

IV. Conjugate.

0.1 ml horseradish peroxidase tagged anti-hepatitis A-F(ab')$_2$ conjugate, diluted in PBS/tween+5% negative human serum was pipetted into the wells, and the whole was incubated for 1 hour at 37° C., followed by washing 5× with PBS/Tween.

V. Substrate.

1 tablet ortho-phenylene diamine was dissolved in 30 ml distilled water (A).

1 tablet urea peroxide was dissolved in 7.5 ml distilled water (B).

0.5 ml (B) was added to 30 ml (A).

0.1 ml of this mixture was pipetted into each well and incubated in the dark for 45 minutes at room temperature.

The enzyme-substrate reaction was stopped with 0.05 ml 4 N sulphuric acid.

Ortho-phenylene diamine and urea peroxide originated from a Hepanostika test kit for the determination of hepatitis B surface antigen, Organon Teknika, Oss, Holland.

VI. Measurement of color change.

The color change of the substrate per well was measured at a wavelength of 492 nm, with the aid of a Vitatron photometer.

VII. Interpretation.

5 negative controls were determined with each set of estimations. The mean extinction of these 5 controls+5× standard deviation served as the boundary between negative and positive sera.

EXAMPLE II

The interference of rheumatoid factor (RF) was investigated in a comparative test for the determination of anti-hepatitis A virus IgM antibodies (anti-HAV-IgM). A series of twenty RF positive sera, some of them containing also anti-hepatitis A virus IgG antibodies (anti-HAV-IgG), were tested with the test system as described in Example I.E., with the exception that besides the conjugate anti-HAV-F(ab')$_2$-HRP, as described in I.E.IV. also anti-HAV-Ig-HRP and anti-HAV-IgG-HRP are used in parallel tests. The latter conjugates have been prepared analogue to the method, described for anti-HAV-F(ab')$_2$-HRP in I.D.

No IgM antibodies were present in the test series, in which the F(ab')$_2$-HRP conjugate according to the invention is used. The Ig-HRP and IgG-HRP conjugates gave a lot of false positive results.

Furthermore from the Ig fraction of this series of RF positive sera the IgG and IgM fractions have been isolated with sucrose gradient centrifugation and these fractions are tested separately in an anti-HAV-enzyme immuno-assay. It could herewith confirmed, that no anti-HAV IgM antibodies were present.

The results are given in the table below. A sample was considered positive if the absorption, measured at 492 nm, after substrate addition, was higher than 2,1 times the absorbance of a negative control. The RF content is indicated with the reciprocal RF titer, determined according to Rose-Waaler's test.

| Serum | Reciprocal RF-titer (Rose-Waaler) | Result total anti-HAV-ELISA Sucrose fraction IgG | Result total anti-HAV-ELISA Sucrose fraction IgM | Result in anti-HAV-IgM test (ELISA) Ig-HRP | Result in anti-HAV-IgM test (ELISA) IgG HRP | Result in anti-HAV-IgM test (ELISA) F(ab')$_2$-HRP |
| --- | --- | --- | --- | --- | --- | --- |
| 1 | 16 | − | − | − | − | − |
| 2 | 32 | + | − | − | + | − |
| 3 | 32 | − | − | − | − | − |
| 4 | 64 | + | − | − | + | − |
| 5 | 64 | + | − | + | + | − |
| 6 | 64 | + | − | − | + | − |
| 7 | 128 | − | − | − | + | − |
| 8 | 128 | − | − | − | + | − |
| 9 | 128 | + | − | − | + | − |
| 10 | 256 | + | − | + | + | − |
| 11 | 256 | + | − | − | + | − |
| 12 | 512 | + | − | + | + | − |
| 13 | 512 | + | − | + | + | − |
| 14 | 512 | − | − | − | + | − |
| 15 | 1024 | − | − | − | + | − |
| 16 | 1024 | + | − | + | + | − |
| 17 | 2048 | − | − | − | + | − |
| 18 | 2048 | − | − | + | + | − |
| 19 | 2048 | − | − | + | + | − |
| 20 | 2048 | + | − | + | + | − |
| Pos. Control | | − | + | + | + | + |
| Neg. Control 1 | | | | − | − | − |
| Neg. Control 2 | | | | − | − | − |

EXAMPLE III

Enzyme Immuno Assay for the detection and determination of human toxoplasma IgM-antibodies A. Preparation of anti-human IgM A sheep was immunized with human IgM prepared from a Waldenström's macroglobulinaemia serum. The specificity of the antiserum was improved by absorption with human cord serum, which procedure removed the anti IgG-activity of the antiserum. 1 ml of sheep anti human IgM serum was mixed with 0.5 ml human cord serum and incubated for 1 hour at 37° C. The mixture was centrifuged for 10 min. at 8,000 g. The supernatant was used as the anti-IgM serum; it was stored at 4° C.

B. Preparation of toxoplasma antigen

Toxoplasma gondii parasites were grown in the intraperitoneal cavity of mice for 3 days. The cells were harvested after killing the mice by rinsing the cavity with 1 ml phosphate-buffered saline (PBS) pH 7.2. A suspension of the cells in PBS was sonicated for 5 minutes with low intensity. Intact parasite cells were collected by centrifugation, resuspended in PBS pH 7.2 and sonicated with high intensity for 10 minutes. This suspension was used as an antigen preparation. It was frozen and stored at −20° C.

C. Preparation of fragments (F(ab')$_2$) of IgG directed against toxoplasma antigen.

A sheep was immunized with 1 mg of above mentioned toxoplasma antigen preparation. The serum was collected and the IgG was isolated by the caprilic acid method according to M. Steinbuch and R. Audran (Arch. Biochem, & Biophysics 134, 279–284 (1969)).

F(ab')$_2$-fragments were prepared by incubation of the IgG solution with pepsin in a 0.1 M acetate buffer pH 4,3 with a pepsin/IgG ratio of 1/50 for 8 hours at 37° C. The reaction was stopped by raising the pH to 8 by addition of sufficient solid tris(hydroxymethyl)-amino methane. The fragments were purified by gel-chromatography on a Sephacryl S 200 column in 0.1 M TRIS/HCl pH 7.5 +0.2 M NaCl+0.002 M EDTA.

D. Preparation of enzyme labelled F(ab')$_2$-fragment (conjugate)

Preparation of the F(ab')$_2$-conjugate was performed according to the method mentioned in Example I.D.

E. Detection of IgM antibodies against toxoplasma gondii; assay procedure.

I. Coating

The wells of polyvinylchloride microtitre plates were coated by adding a dilution of 1/10,000 of sheep anti human IgM serum in 0.05 M $Na_2CO_3$/HCl buffer at pH 9.0 and incubating for 16 hours at room temperature. Hereafter the wells were washed three times with PBS (pH 7.2), containing 0.05% Tween 20 (PBS-Tween).

II. Serum

Then 0.1 ml of an appropriate dilution of the test serum in PBS Tween was added and the wells were incubated for 4 hours at 37° C. Hereafter the wells were washed 3 times with PBS Tween.

III. Antigen

The wells were incubated for 16 hours at room temperature with 0.1 ml of a suitable dilution of the antigen solution in PBS Tween. Hereafter the wells were washed 4 times with PBS Tween.

IV. Conjugate

Then 0.1 ml of an appropriate dilution of anti-toxoplasma F(ab')$_2$-conjugate in PBS Tween was added and the wells were incubated for 1 hour at 37° C. Hereafter the wells were washed 5 times with PBS Tween.

V. Substrate

The substrate solution was prepared according to the method of Example I.V. 0.1 ml substrate solution was pipetted into each cup and incubated for 30 minutes at room temperature in the dark. The reaction was stopped by adding 0.1 ml of 4 N $H_2SO_4$ to the wells.

VI. Measurement of color change

The color development in the wells was measured as the extinction of the substrate solution at 492 nm in a Vitatron photometer.

VII. Interpretation of results

Together with each set of estimations 5 negative controls were tested simultaneously. A value of 2.1 times the mean extinction of these negative controls was taken as the boundary between positive and negative results.

EXAMPLE IV

Detection of IgG antibodies against rubella virus/antigen

A. Preparation of anti-human IgG serum

Rabbit anti-human IgG was prepared by injection of 0.5 mg purified human IgG into rabbits, followed by a booster injection of 0.5 mg IgG two months later. One week later the rabbits were bled and the serum was collected, and stored at −20° C. until use.

B. Preparation of rubella virus/antigen

Rubella virus M 33 strain was produced in BHK 21 cells cultured as a monolayer. Antigens were isolated by ultrasonication of the cells in a glycine/NaOH buffer H 9.0. The suspension was centrifuged for 30 minutes at 3,000 g; the supernatant served as an antigen solution.

C. Preparation of F(ab')$_2$-fragments of IgG against rubella

IgG was isolated from a human anti-rubella serum by caprilic acid precipitation of other serum-components. IgG in the supernatant was dialysed against 0.1 M NaAc/HAc buffer at pH 4.3. Pepsin was dissolved in the same buffer, and added to give a pepsin:IgG ratio of 1:50. The mixture was incubated for eight hours at 37° C.; the reaction was stopped by raising the pH to 8 with solid tris(hydroxymethyl)-amino methane. F(ab')$_2$-fragments were purified on a Sephacryl S 200 column in 0.1 M TRIS/HCl pH 7.5+0.9% NaCl.

D. Preparation of enzyme-labelled F(ab')$_2$

F(ab')$_2$ conjugate was prepared according to the method described in Example I.D.

E. Determination of IgG antibodies against rubella in human serum

I. Coating

The wells of polystyrene microtitre plates were coated with F(ab')$_2$ fragments of rabbit-anti-human IgG, by incubation of 0.1 ml F(ab')$_2$ solution in 0.05 M phosphate buffer, pH 7.2 (PBS) for 1 night at room temperature. After incubation the wells were washed with PBS+0.05% Tween 20 (pH 7.2).

II. Test serum 0.1 ml of several dilutions of test serum in PBS Tween pH 7.2 were incubated for 2 hours at 37° C. Afterwards the wells were washed 3 times with PBS Tween (pH 7.2). Positive and negative control sera were tested simultaneously.

III. Antigen 0.1 ml of a dilution of the rubella antigen solution in PBS-Tween with pH 7.2 was incubated for 16 hours at room temperature. Afterwards the wells were washed 3 times with PBS-Tween (pH 7.2).

IV. Conjugate 0.1 ml F(ab')$_2$ anti-rubella conjugate, diluted in PBS Tween pH 7.2, was incubated for 1 hour at 37° C. Afterwards the wells were washed 5 times with PBS-Tween (pH 7.2).

V. Substrate

A solution of ortho-phenylene-diamine mixed with a solution of urea-peroxide was used as substrate. 0.1 ml of the substrate solution was incubated for 30 minutes at room temperature; the reaction was stopped by addition of 0.1 ml 4 N $H_2SO_4$.

VI. Measuring color change

The change of color in the wells was measured by measuring the extinction of the substrate solutions in the wells with a Vitatron photometer at a wavelength of 492 nm.

VII. Interpretation

The dilutions of the test sera that gave extinctions of 50% of the positive control were taken as the antibody titres of the sera.

What is claimed is:

1. Method for the detection or determination of an antigen specific immunoglobulin of a predetermined IgX class in a test medium wherein X is selected from the group consisting of M, A, D and E, comprising:
    (a) contacting and reacting the test medium with either insolubilized anti-IgX against the antigen specific immunoglobulin of the peculiar IgX class to be detected or determined, or antigen binding fragment of said anti-IgX under conditions suitable for forming a reaction product of said insolubilized anti-IgX bound to said IgX;
    (b) incubating said contacted and reacted test medium with an antigen for which the immunoglobulin to be detected or determined has specific affinity, and with a labelled antigen binding fragment of an antibody against said antigen; and
    (c) detecting or determining the labelling fragment, which detection or determination provides qualitative or quantitative information about the antigen specific immunoglobulin to be detected or determined.

2. Method according to claim 1, wherein a separation is performed after contacting and reacting the test medium with the insolubilized anti-IgX or antigen binding fragment of this anti-IgX.

3. Method according to claim 1 or 2, wherein after the test medium has been contacted and reacted with the insolubilized anti-IgX or antigen binding fragment of this anti-IgX, a coupling product consisting essentially of the antigen immunochemically bound to a labelled antigen binding fragment of an antibody against said antigen is added to the test medium or the insolubilized phase.

4. Test kit for the detection or determination of an antigen specific immunoglobulin of a peculiar IgX class according to the method of claim 3, comprising:
   (a) insolubilized anti-IgX against the antigen specific immunoglobulin of a peculiar IgX class to be detected or determined, or an antigen binding fragment of this anti-IgX;
   (b) a coupling product of an antigen, for which the immunoglobulin to be detected or determined has specific affinity, immunochemically bound to a labelled antigen binding fragment of an antibody against the antigen concerned; and
   (c) directions for the performance of said method.

5. Method according to claim 1, wherein the labelled antibody fragment is a labelled F(ab')$_2$ fragment.

6. Method according to claim 1, wherein the labelled antibody fragment is labelled with an enzyme.

7. Test kit for the detection or determination of an antigen specific immunoglobulin of a peculiar IgX class according to the method of claim 1, comprising:
   (a) insolubilized anti-IgX against the antigen specific immunoglobulin of a peculiar IgX class to be detected or determined, or an antigen binding fragment of this anti-IgX;
   (b) an antigen, for which the IgX immunoglobulin to be determined has a specific affinity;
   (c) a labelled antigen binding fragment of an antibody against said antigen (b); and
   (d) directions for the performance of said method.

8. Test kit according to claim 7, in which the labelling agent is an enzyme.

9. Test kit according to claim 8, which contains also a substrate for said enzyme.

10. A diagnostic test kit for performing the method of claim 1, comprising:
    (a) a given quantity of an insolubilized anti-antibody, or fragments thereof, against the IgX immunoglobulin to be detected or determined;
    (b) a given quantity of a specific binding antigen against the IgX immunoglobulin to be detected or determined;
    (c) a given quantity of a labeled Fab-antibody against the specific binding antigen of step (b);
    (d) directions for the performance of said method; and
    (e) a container for housing (a)–(d).

11. The test kit of claim 10, wherein the label is an enzyme, and the test kit also contains a substrate for the enzyme used.

12. Method for the detection or determination of an antigen specific immunoglobulin of the IgM class in a test medium, comprising:
    (a) contacting and reacting the test medium with insolubilized anti-IgM against the antigen specific immunoglobulin of the IgM class to be detected or determined under conditions suitable for forming a reaction product of said insolubilized anti-IgM bound to said IgM;
    (b) incubating said contacted and reacted test medium with an antigen for which the immunoglobulin to be detected or determined has specific affinity, and with a labelled antigen binding fragment of an antibody against said antigen; and
    (c) detecting or determining the labelling fragment, which detection or determination provides qualitative or quantitative information about the antigen specific immunoglobulin to be detected or determined.

13. A method for the detection of an IgX immunoglobulin in a serum sample containing the immunoglobulin, wherein X is selected from the group consisting of M, A, D and E, comprising the steps of:
    (a) providing a given quantity of an insolubilized anti-antibody, or fragments thereof, against the IgX immunoglobulin to be detected;
    (b) contacting and incubating a given quantity of the liquid serum having the IgX immunoglobulin to be detected with said reagent of step (a), to form a first liquid phase and a first solid phase;
    (c) separating the first solid phase from the first liquid phase;
    (d) contacting and incubating with said first phase a given quantity of a specific binding antigen for which the IgX immunoglobulin to be detected has specific binding affinity, in order to form a second solid phase and a second liquid phase;
    (e) separating the solid phase of the second reaction mixture from the second liquid phase;
    (f) contacting and incubating said solid phase of the second reaction mixture with a given quantity of a labeled Fab-antibody against the specific binding antigen, in order to form a third solid phase and a third liquid phase; and
    (g) detecting the labeled activity of either the third liquid phase or the third solid phase of step (f) after separating said phases, which detection is a measure of the presence of the component to be detected.

14. The method of claim 13, wherein the label is an enzyme.

15. The method of claim 13, where IgX is an IgM antibody against hepatitis A virus antigen.

16. The method of claim 13, wherein the insolubilized anti-antibody of step (a) is at least immunochemically equivalent to the maximum amount of IgX expected.

17. The method of claim 16, wherein the specific binding antigen of step (d) is at least immunochemically equivalent to the insolubilized anti-antibody of step (a), and the labeled Fab-antibody of step (f) is at least immunochemically equivalent to the specific binding antigen of step (d).

18. The method of claim 13, wherein the separation steps are performed by aspiration and washing with water.

19. The method of claim 13, wherein the label is an enzyme.

20. The method of claim 13, wherein IgX is an IgM antibody against hepatitis A virus antigen.

21. The method of claim 13, wherein the separation steps are performed by aspiration and washing with water.

22. A method for the detection and determination of an IgX immunoglobulin in an serum sample containing the IgX immunoglobulin, wherein X is selected from the group consisting of M, A, D and E, comprising the steps of:
(a) providing a given quantity of an insolubilized anti-antibody, or fragments thereof, against the IgX immunoglobulin to be detected and determined;
(b) contacting and incubating a given quantity of the serum having the IgX immunoglobulin to be detected and to be determined with said reagent of step (a), whereby the reagent of step (a) is at least immunochemically equivalent to the maximum amount of IgX immunoglobulin expected, forming a reaction mixture having a first solid phase and a first liquid phase;
(c) separating the first solid phase from the first liquid phase;
(d) contacting and incubating with said first solid phase a given quantity of a specific binding antigen for which the IgX immunoglobulin to be detected and determined has specific binding affinity, whereby the specific binding antigen is at least immunochemically equivalent to the insolubilized anti-antibody of step (a), in order to form a second reaction mixture having a second solid phase and a second liquid phase;
(e) separating the solid phase of the second reaction mixture from the second liquid phase;
(f) contacting and incubating said solid phase of the second reaction mixture with a given quantity of a labeled Fab-antibody against the specific binding antigen, wherein the labeled Fab-antibody is at least immunochemically equivalent to the specific binding antigen of step (d), in order to form a third solid phase and a third liquid phase; and
(g) detecting and determining the labeled activity of either the third liquid phase or the third solid phase of step (f) after separating said phases, which detection and determination is a measure of the presence and quantity of the component to be detected and determined.

23. The method of claim 13 or claim 22 wherein the insolubilized Fab antibody is water-insoluble and water-insuspensible.

24. A diagnostic test kit for performing the method of claim 22, comprising:
(a) a given quantity of an insolubilized anti-antibody, or fragments thereof, against the IgX immunoglobulin to be detected and to be determined, which quantity is at least immunochemically equivalent to the maximum amount of IgX immunoglobulin expected;
(b) a given quantity of a specific binding antigen against the IgX immunoglobulin to be detected and to be determined, which quantity is at least immunochemically equivalent to the insolubilized anti-antibody of step (a);
(c) a given quantity of a labeled Fab-antibody against the specific binding antigen of step (b), which quantity of labeled Fab-antibody is at least immunochemically equivalent to the specific binding antigen of step (b);
(d) directions for the performance of said method; and
(e) a container for housing (a)-(d).

25. The test kit of claim 24, wherein the label is an enzyme, and the test kit also contains a substrate for the enzyme used.

26. A method for the detection of an IgX immunoglobulin in a serum sample containing the IgX immunoglobulin, wherein X is selected from the group consisting of M, A, D and E, comprising the steps of:
(a) providing a given quantity of an insolubilized anti-antibody, or fragments thereof, against the IgX immunoglobulin to be detected;
(b) contacting and incubating a given quantity of the liquid serum having the IgX immunoglobulin to be detected with said reagent of step (a);
(c) separating the solid phase from the liquid phase;
(d) contacting and incubating with said solid phase a given quantity of a labeled reagent, which labelled reagent consists essentially of:
(1) a specific binding antigen against the IgX immunoglobulin to be detected, which antigen is immunochemically bound to
(2) a Fab-labeled antibody against said specific binding antigen,
to form a second solid phase and a second liquid phase; and
(e) detecting the labeled activity of either the second solid phase or second liquid phase of step (d) after separating said phases, which detection is a measure of the presence of the component to be detected.

27. A diagnostic test kit for performing the method of claim 26, comprising:
(a) a given quantity of an insolubilized anti-antibody, or fragments thereof, against the IgX immunoglobulin to be detected;
(b) a given quantity of a labeled reagent, which labeled reagent consists essentially of:
(1) a specific binding antigen against the IgX immunoglobulin to be detected, which antigen is immunochemically bound to
(2) a Fab-labeled antibody against said specific binding antigen;
(c) directions for the performance of said method; and
(d) a container for housing (a)-(d).

28. A method for the detection and determination of an IgX immunoglobulin in a serum sample containing the IgX immunoglobulin, wherein X is selected from the group consisting of M, A, D and E, comprising the steps of:
(a) providing a given quantity of an insolubilized anti-antibody, or fragments thereof, against the IgX immunoglobulin to be detected and to be determined;
(b) contacting and incubating a given quantity of the liquid sample having the IgX immunoglobulin to be detected and to be determined with said reagent of step (a), whereby the quantity of the reagent of step (a) is at least immunochemically equivalent to the maximum amount of IgX immunoglobulin expected, forming a reaction mixture having a solid phase and a liquid phase;
(c) separating the solid phase from the liquid phase;
(d) contacting and incubating with said solid phase a given quantity of a labeled reagent, which quantity is at least immunochemically equivalent to the insolubilized anti-antibody of step (a), which labeled reagent consists essentially of:
(1) a specific binding antigen against the IgX immunoglobulin to be detected and to be determined, which antigen is immunochemically bound to (2) a Fab-labeled antibody against said specific binding antigen;

to form a second solid phase and a second liquid phase; and (e) detecting and determining the labeled activity of either the second solid phase or the second liquid phase of step (d) after separating said phases, which detection and determination is a measure of the presence and quantity of the component to be detected and determined.

29. The method of claim 26 or 28, wherein an enzyme is employed for the label.

30. A diagnostic test kit for performing the method of claim 28, comprising:

(a) a given quantity of an insolubilized anti-antibody, or fragments thereof, against the immunoglobulin IgX to be detected and to be determined, which quantity is at least immunochemically equivalent to the maximum amount of IgX immunoglobulin expected;

(b) a given amount of a labeled reagent which quantity is at least immunochemically equivalent to the insolubilized anti-antibody of step (a), which labeled reagent consists essentially of:

(1) a specific binding antigen against the IgX immunoglobulin to be detected and to be determined, which antigen is immunochemically bound to (2) a Fab-labeled antibody against said specific binding antigen;

(c) directions for the performance of said method; and (d) a container for housing (a)–(d).

31. A test kit according to claims 27 or 30, wherein the label is an enzyme, and the test kit also contains a substrate for the enzyme concerned.

* * * * *